(12) United States Patent
Akiyama et al.

(10) Patent No.: US 6,428,813 B1
(45) Date of Patent: Aug. 6, 2002

(54) GASTROINTESTINAL MUCOSA-ADHERENT PHARMACEUTICAL COMPOSITION

(75) Inventors: Yohko Akiyama, Ohmihachiman; Naoki Nagahara, Itami; Megumi Kitano, Nishinomiya; Masafumi Nakao, Ikoma, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/380,939

(22) PCT Filed: Mar. 24, 1998

(86) PCT No.: PCT/JP98/01284

§ 371 (c)(1), (2), (4) Date: Sep. 10, 1999

(87) PCT Pub. No.: WO98/42311

PCT Pub. Date: Oct. 1, 1998

(30) Foreign Application Priority Data

Mar. 25, 1997 (JP) ................................. 9-071408

(51) Int. Cl.⁷ .............................. A61K 9/10; A61K 9/16; A61K 47/32; A61K 47/38
(52) U.S. Cl. ...................... 424/501; 424/499; 424/485; 424/487
(58) Field of Search ................................. 514/345, 944, 514/777, 781, 778, 925–27; 424/488, 484, 489, 499, 502

(56) References Cited

U.S. PATENT DOCUMENTS

| | | | |
|---|---|---|---|
| 5,576,025 A | * 11/1996 | Akiyama et al. | |
| 5,654,009 A | * 8/1997 | Hata et al. | |
| 5,731,006 A | 3/1998 | Akiyama et al. | |
| 5,840,917 A | 11/1998 | Oi et al. | |
| 5,851,809 A | * 12/1998 | Lawlor | |
| 5,948,773 A | 9/1999 | Akiyama et al. | |

FOREIGN PATENT DOCUMENTS

| | | |
|---|---|---|
| EP | 0250 374 A | 12/1987 |
| EP | 0514 008 A | 11/1992 |
| EP | 0642 797 A | 3/1995 |
| EP | 0793 959 A | 9/1997 |
| JP | 09 268 126 A | 10/1997 |
| WO | WO 93 15746 A | 8/1993 |
| WO | WO 94 00112 A | 1/1994 |

* cited by examiner

*Primary Examiner*—Edward J. Webman
(74) *Attorney, Agent, or Firm*—Mark Chao; Elaine M. Ramesh

(57) ABSTRACT

In order to provide a composition having a long gastroduodenal residence time and exhibiting an improved efficacy, is provided a gastrointestinal mucosa-adherent composition comprising an active ingredient and a material which swells a viscogenic agent capable of being viscous with water a (e.g. curdlan and/or a low-substituted hydroxypropylcellulose etc.).

27 Claims, No Drawings

GASTROINTESTINAL MUCOSA-ADHERENT PHARMACEUTICAL COMPOSITION

This is a 371 of PCT/JP98/01284 filed Mar. 24, 1998.

BACKGROUND ART

Since 1983 when *Helicobacter pylori* (hereinafter sometimes abbreviated as *H. Pylori* or HP) was first isolated [Lancet, 1, 1273 (1983)], its relation to gastritis and gastrointestinal ulcer has gathered attention. This is because whereas HP is not usually found in the gastric mucus and on the gastric epithelium of healthy humans [APMIS, 96, 84 (1983)], it is detected at a high rate among patients with chronic gastritis or gastric ulcer. [Am. J. Gastroenterol., 32, 2283 (1987)].

The cure rate of gastroduodenal ulcer rose phenomenally with the development of $H_2$ blockers and proton pump inhibitors (briefly, PPI). However there still are refractory cases not even responding to judicious treatments with those drugs, thus posing a serious problem. According to a report reviewing such refractory gastric ulcer cases [Japanese Journal of Gastroenterology, 89, 571 (1992)], depressions were found in the amount of gastric mucus, because of apparently the ammonia produced by HP. It has also been reported that a sustained HP infection retards healing of the ulcer or is involved in relapses of the ulcer [Lancet, 335, 1233 (1990); N. Engl. J. Med., 328, 308 (1993)]. Heretofore, various drugs having anti-*Helicobacter pylori* activity have been administered to patients with gastroduodenal ulcers. For example, as antimicrobial preparations against *Helicobacter pylori*, amoxicillin, metronidazole, bismuth nitrate, and tetracycline are administered either independently or in combination, but because their effective doses are comparatively high (e.g. 750 mg amoxicillin or 500 mg metronidazole, to be administered three times daily), those preparations frequently entail side effects such as diarrhea, abdominal pain, and nausea.

Meanwhile, in order to maintain its life, *Helicobacter pylori* is obliged to decompose urea into ammonia with the urease which it elaborates for itself. Therefore, urease inhibitors such as hydroxamic acid derivatives (the 15th Medical Chemistry Symposium, Synopsis of Lectures at the 4th Annual Meeting of Medical Chemistry Group, page 167, P-41), a cassia bark extract [Synopsis of Lectures at the 117th Congress of Pharmaceutical Society of Japan 27 [H1] 9-5, p81 (1997)], and flurofamide [Micro. Ecol. Health Dis., 4 (Suppl.) S145 (1991)] are expected to have anti-*Helicobacter pylori* activity.

For an improved expression of the efficacy of a active ingredient and a reduced risk for side effects, an attempt was made to formulate amoxicillin, for instance, into a gastric mucosa-adherent composition to prolong its intragastric residence time and let amoxicillin be released at a controlled rate and with consequent improved availability of active ingredient (WO 94/00112). It has been demonstrated that the rate of clearance of *Helicobacter pylori* can be improved by causing an anti-HP substance to stay in the stomach longer to ensure prolonged exposure of the bacteria to the active substance [Scand. J. Gastroenterol., 29, 16–42 (1994)].

A combination drug delivery system has also been constructed, in which an antimicrobial substance and/or an antiulcer substance is supplied in a gastric mucosa-adherent solid composition. It has been shown that with this drug delivery system,,the efficacy of the antimicrobial substance and that of the antiulcerative substance can be synergistically exploited (Japanese Patent Unexamined Publication No. 126189/1995).

The present invention has for its object to provide a pharmaceutical composition which has enhanced mucosa-adherent activity compared with other gastric mucosa-adherent preparations, and consequently, an extremely improved efficacy of the active ingredient, in particular, an anti-*Helicobacter pylori* composition and a pharmaceutical preparation, for the prophylaxis, treatment or prevention of relapse of gastroduodenal ulcers, which is very satisfactory and favorable in having anti-HP effect, low risk for side effects, sustained effect, and safety.

DISCLOSURE OF INVENTION

In view of the above state of the art, the inventors of the present invention have discovered that the effectiveness of active ingredients (e.g. anti HP effect) can be potentiated by incorporating an agent (e.g. a curdlan and/or a low-substituted hydroxypropylcellulose) which swells a viscogenic agent, in the objective gastrointestinal mucosa-adherent composition containing an active ingredient (e.g. anti HP substance), and that the composition has favorable safety characteristics and an enhanced adhesion the mucosa.

The present invention, therefore, is directed to:

(1) A gastrointestinal mucosa-adherent pharmaceutical composition comprising a material which swells a viscogenic agent capable of being viscous with water (viscogenic agent), (2) A pharmaceutical composition according to (1), wherein the material is a curdlan and/or a low-substituted hydroxypropylcellulose, (3) A pharmaceutical composition according to (2), which is matrix comprising a polyglycerol fatty acid ester and/or a lipid, (4) A pharmaceutical composition according to (3), wherein the curdlan and/or the low-substituted hydroxypropylcellulose is dispersed, (5) A pharmaceutical composition according to (4), which is in a granule form, (6) A pharmaceutical composition according to (1), which is an anti-*Helicobacter pylori* preparation, (7) A pharmaceutical composition according to (1), which is an antimicrobial preparation, (8) A pharmaceutical composition according to (2), wherein the hydroxypropoxy content of the low-substituted hydroxypropylcellulose is about 7.0 to about 13.0%, (9) A pharmaceutical composition according to (3), wherein the lipid is a hydrogenated castor oil,

(10) A pharmaceutical composition according to (3), wherein the polyglycerol fatty acid ester is an ester of a polyglycerol having a degree of polymerization from about 2 to about 20 with a fatty acid containing about 8 to about 40 carbon atoms.

(11) A pharmaceutical composition according to (3), wherein the amount of the polyglycerol fatty acid ester and/or the lipid used is about 20 to about 95 weight % to the total weight of the composition,

(12) A pharmaceutical composition according to (3), wherein the amount of the polyglycerol fatty acid ester and/or the lipid used is about 0.1 to about 100 times by weight to the active ingredient in the composition,

(13) A pharmaceutical composition according to (3), comprising a viscogenic agent in the matrix,

(14) A pharmaceutical composition according to (12), wherein the amount of the viscogenic agent used is about 0.5 to about 45 weight % to the total weight of the composition,

(15) A pharmaceutical composition according to (3), wherein the HLB number of the polyglycerol fatty acid ester is about 1 to about 9,

(16) A pharmaceutical composition according to (6), wherein the amount of the anti-*Helicobacter pylori* substance used is about 10 to about 50 weight % to the total weight of the composition,

(17) A pharmaceutical composition according to (3), wherein the matrix is coated with a coating material comprising a viscogenic agent,

(18) A pharmaceutical composition according to (13) or (17), wherein the viscogenic agent is an acrylic polymer or salt thereof,

(19) A pharmaceutical composition according to (6), wherein the anti-*Helicobacter pylori* substance is amoxicillin,

(20) A pharmaceutical composition according to (6), wherein the anti-*Helicobacter pylori* substance is N-(diaminophosphinyl)-5-methyl-2-thiophenecarboxamide,

(21) A pharmaceutical composition according to (6), wherein the anti-*Helicobacter pylori* substance is a tryptophanyl-t-RNA synthesis inhibitor,

(22) A pharmaceutical composition according to (6), wherein the anti-*Helicobacter pylori* substance is a oxazolone derivative,

(23) A pharmaceutical composition according to (6), wherein the anti-*Helicobacter pylori* substance is indolmycin,

(24) An accelerant of gastrointestinal mucosa-adherent activity of a gastrointestinal mucosa-adherent composition, comprising a curdlan and/or a low-substituted hydroxypropylcellulose,

(25) A method to accelerate gastrointestinal mucosa-adherent activity by using a curdlan and/or a low-substituted hydroxypropylcellulose,

(26) A use of the curdlan and/or a low-substituted hydroxypropylcellulose as an accelerant of gastrointestinal mucosa-adherent activity of a gastrointestinal mucosa-adherent composition,

(27) A pharmaceutical composition according to (6), which is a composition for the prophylaxis, treatment, or prevention of relapse of *Helicobacter pylori* related disease,

(28) A pharmaceutical composition according to (3), comprising (i) the low-substituted hydroxypropylcellulose, (ii) the acrylic polymer or salt thereof, (iii) the polyglycerol fatty acid ester and/or the lipid, and (iv) an anti-*Helicobacter pylori* substance,

(29) A pharmaceutical composition according to (28), wherein (i) the hydroxypropoxy content of the low-substituted hydroxypropylcellulose is about 7.0 to about 13.0%, (ii) the molecular weight of the acrylic polymer is about $20 \times 10^4$ to about $600 \times 10^4$, (iii) the polyglycerol fatty acid ester and/or the lipid is tetraglycerol polyricinolate, and (iv) the anti-*Helicobacter pylori* substance is indolmycin, and

(30) A pharmaceutical composition according to (3), comprising (i) about 1 to about 20 parts by weight of the low-substituted hydroxypropylcellulose, whose hydroxypropoxy content is about 7.0 to about 13.0%, (ii) about 1 to about 20 parts by weight of the acrylic polymer or salt thereof, whose molecular weight is about $20 \times 10^4$ to about $600 \times 10^4$, (iii) about 40 to about 90 parts by weight of the behenic acid hexa(tetra) glyceride and/or tetraglycerol polyricinolate, and (iv) about 5 to about 40 parts by weight of indolmycin.

DETAILED DESCRIPTION

The gastrointestinal mucosa-adhesive composition according to the present invention is, for instance, a composition comprising an active ingredient having such as anti-HP activity (for example, an antimicrobial substance or an urease inhibitor) and a material which swells a viscogenic agent (e.g. either a curdlan or a low-substituted hydroxypropylcellulose or both). The composition is at least adapted to attach itself to the gastrointestinal mucosa (at least gastric mucosa) and/or otherwise stay in the gastrointestine (at least stomach) and release the active ingredient such as anti-HP substance contained therein at a suitable rate and thereby display a potentiated pharmaceutical effect (e.g. anti-HP action).

An example of the above-mentioned composition would be a composition comprising (a) an anti-HP substance as a typical active ingredient and (d) a viscogenic agent capable of being viscous with water (hereinafter sometimes referred to as a viscogenic agent) and also (b) a curdlan and/or a low-substituted hydroxypropylcellulose as a swelling material and preferably be a composition further comprising (c) a polyglycerol fatty acid ester and/or a lipid. Though there is no particular limitation on its dosage form, the composition is preferably a solid composition and particularly a composition containing a matrix. The matrix may, for example, be a gastrointestinal mucosa-adhesive matrix comprising (c) a polyglycerol fatty acid ester and (d) a viscogenic agent in addition to (a) and (b) or a gastrointestinal mucosa-adhesive matrix comprising (c) a lipid and (d) a viscogenic agent in addition to (a) and (b). The preferred matrix is a gastrointestinal mucosa-adhesive matrix comprising (c) a polyglycerol fatty acid ester and (d) a viscogenic agent.

The gastrointestinal mucosa-adhesive matrix comprising said four components (a), (b), (c), and (d) is preferably a matrix such that the viscogenic agent is dispersed in the matrix which comprises the polyglycerol fatty acid ester or lipid or a matrix which is covered with the viscogenic agent. The melting point of the gastrointestinal mucosa-adhesive matrix may, for example, be about 30° to about 120° C. and preferably about 40° to about 120° C.

The polyglycerol fatty acid ester for use in the present invention is esters of polyglycerols with fatty acids and may be a mono- to polyester (diester, triester, etc.). The polyglycerol fatty acid ester is characterized in that it does not undergo polymorphic transition or any material interaction with the active ingredient, allowing those coexisting ingredients to remain undeactivated and stable for an extended period of time.

Polyglycerol by definition is "a polyhydric alcohol containing n (cyclic form,) to (n+2) (straight-chain form or branched form) hydroxyl groups and (n−1) (straight-chain form or branched form) to n (cyclic) ether bonds per molecule" [Polyglycerin Esters, (ed.) Sakamoto Yakuhin Kogyo Co., Ltd., published Oct. 4, 1994), and any straight-chain ester or branched-chain ester can be used in the present invention.

For example, compounds of the following formula (I) can be employed.

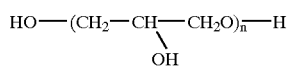

$$HO-(CH_2-CH-CH_2O)_{\overline{n}}-H \quad \quad (I)$$
$$\qquad\qquad\;\;|$$
$$\qquad\qquad\;OH$$

(wherein n represents a degree of polymerization which is an integer of not less than 2). The value of n is generally about 2 to about 50, preferably about 2 to about 20, and for still better results, about 2 to about 10.

The polyglycerol includes but is not limited to diglycerol, triglycerol, tetraglycerol, pentaglycerol, hexaglycerol, heptaglycerol, octaglycerol, nonaglycerol, decaglycerol, pentadecaglycerol, eicosaglycerol, and triacontaglycerol. Among those polyglycerols, tetraglycerol, hexaglycerol or decaglycerol is used in many cases.

The fatty acid includes but is not limited to saturated or unsaturated fatty acids each containing about 8 to about 40, preferably about 12 to about 25, and more preferably about 15 to about 22 carbon atoms. The preferred fatty acid is stearic acid, oleic acid, lauric acid, linoleic acid, linolenic acid, ricinoleic acid, caprylic acid, capric acid, or behenic acid.

The polyglycerol fatty acid ester includes but is not limited to behenic acid hexa(tetra)glyceride, caprylic acid mono(deca)glyceride, caprylic acid di(tri)glyceride, capric acid di(tri)glyceride, lauric acid mono(tetra)glyceride, lauric acid mono (hexa)glyceride, lauric acid mono(deca) glyceride, oleic acid mono(tetra)glyceride, oleic acid mono (hexa)glyceride, oleic acid mono(deca)glyceride, oleic acid di(tri)glyceride, oleic acid di(tetra)glyceride, oleic acid sesqui(deca)glyceride, oleic acid penta(tetra)glyceride, oleic acid penta(hexa)glyceride, oleic acid deca(deca)glyceride, linoleic acid mono(hepta)glyceride, linoleic acid di(tri) glyceride, linoleic acid di(tetra) glyceride, linoleic acid di(hexa)glyceride, stearic acid mono(di)glyceride, stearic acid mono(tetra)glyceride, stearic acid penta(tetra) glyceride, stearic acid mono(deca)glyceride, stearic acid tri(tetra)glyceride, stearic acid penta(hexa) glyceride, stearic acid tri(hexa)glyceride, stearic acid deca(deca) glyceride, palmitic acid mono(tetra)glyceride, palmitic acid mono (hexa)glyceride, palmitic acid mono(deca)glyceride, palmitic acid tri(tetra)glyceride, palmitic acid tri(hexa)glyceride, palmitic acid sesqui(hexa)glyceride, palmitic acid penta (tetra)glyceride, palmitic acid penta(hexa)glyceride, palmitic acid deca(deca)glyceride, and polyglycerol polyricinolate (e.g. tetraglycerol polyricinolate, etc.).

The preferred polyglycerol fatty acid ester includes, for instance, behenic acid hexa(tetra)glyceride (e.g. HB-310™, Sakamoto Yakuhin Kogyo Co., Ltd.,; Poem J-46B™, Riken Vitamin Co.), stearic acid penta(tetra)glyceride (e.g. PS-310™, Sakamoto Yakuhin Kogyo Co., Ltd.), stearic acid mono(tetra)glyceride (e.g. MS-310™, Sakamoto Yakuhin Kogyo Co., Ltd.), stearic acid penta(hexa)glyceride (e.g. PS-500™, Sakamoto Yakuhin Kogyo Co., Ltd.), stearic acid mono(deca)glyceride, polyglycerol polyricinolate (e.g. tetraglycerol polyricinolate, etc.) (e.g. CRS-75™, Sakamoto Yakuhin Co., Ltd.) and mixtures of such glycerides.

Those polyglycerol fatty acid esters can be used each alone or as a mixture of two or more species, preferably about 2 or about 3 species.

The molecular weight of the polyglycerol fatty acid ester is generally about 200 to about 5000, preferably about 300 to about 3000, preferably about 2000 to about 3000. The hydrophile-lipophile balance (HLB) number of the polyglycerol fatty acid ester is generally about 1 to about 22, preferably about 1 to about 15, more preferably about 1 to about 9, for still better results, about 1 to about 4. Two or more polyglycerol fatty acid esters differing in HLB number from each other may be used in combination to provide for the designed HLB number. By adjusting the HLB of the polyglycerol fatty acid ester judiciously, the release and dissolution kinetics of the active drug substance can be controlled as desired.

The proper polyglycerol fatty acid ester can be selected with reference to the particular active ingredient (e.g. anti-HP agent, etc.), viscogenic agent, swelling material (e.g. curdlan, and/or low-substituted hydroxypropylcellulose, etc.), the particular combination thereof, and the objective form of the composition. Preferably, however, compounds which are solid at atmospheric temperature (ca 15° C.) are employed. The melting point of the polyglycerol fatty acid ester may, for example, be about 15 to about 80° C., preferably about 30 to about 75° C., and for still better results, about 45 to about 75° C.

A suitable polyglycerol fatty acid ester is selected according to the species of active ingredient used and the intended dosage form. Generally, polyglycerols with degrees of polymerization in the range of about 2 to about 16 are preferred. The particularly preferred range is about 2 to about 10. Preferred are esters such that the fatty acid has formed an ester bond with at least one of the (degree of polymerization +2) hydroxyl groups, preferably such that the fatty acid or acids have formed ester bonds with not less than about 60%, more preferably not less than about 80%, of the total number of hydroxyl groups in the polyglycerol. The fatty acid or acids are preferably saturated acids each containing about 6 to about 22, more preferably about 15 to about 25, and for still better result, about 18 to about 22 carbon, atoms. The fatty acid involved in the formation of the ester bonds may be of the same kind or different kinds.

In the production of a solid composition according to the present invention by using two or more different polyglycerol fatty acid esters as a mixture, a liquid polyglycerin fatty acid ester may be included in the mixture as long as the final composition is solid at atmospheric temperature.

When the polyglycerol fatty acid ester is used as a gastrointestinal mucosa-adhesive matrix, the amount of the polyglycerol fatty acid ester relative to the total weight of the composition is generally about 5 to about 98 weight %, preferably about 20 to about 95%, more preferably about 40 to about 95% and to the active ingredient in the composition may, for example, be about 0.01 to about 15000 times by weight, preferably about 0.1 to about 1000 times by weight, and for still better result, about 0.1 to about 100 times by weight.

The lipid for use in the present invention is one having a melting point of about 40 to about 120° C., preferably about 40 to about 90° C.

The lipid includes but is not limited to saturated fatty acids of about 14 to about 22 carbon atoms (e.g. myristic acid, stearic acid, palmitic acid, behenic acid, etc.) or salts (sodium salt, potassium salt, etc.) thereof; higher alcohols of about 16 to about 22 carbon atoms (e.g. cetyl alcohol, stearyl alcohol, etc.); fatty acid glycerol esters such as the monoglycerides, diglycerides, triglycerides, etc. of the above-mentioned fatty acids (e.g. 1-monostearate, 1-monopalmitin, etc.); oils (e.g. castor oil, cottonseed oil, beef tallow, etc., inclusive of the corresponding hydrogenated oils); waxes (e.g. beeswax, carnauba wax, sperm wax, etc.); hydrocarbons (e.g. paraffin, microcrystalline wax, etc.); and phospholipids (e.g. hydrogenated lecithin etc.). Among those lipids, oils, waxes, $C_{14-22}$ saturated fatty acids, $C_{16-22}$ higher alcohols, and hydrocarbons are preferred. The more preferred are hydrogenated cottonseed oil, hydrogenated castor oil, hydrogenated soybean oil, carnauba wax, stearic acid, stearyl alcohol, and microcrystalline wax. The most preferred is hydrogenated castor oil or carnauba wax.

When a lipid is used as the gastrointestinal mucosa-adhesive matrix, the amount of the lipid relative to the total weight of the composition is generally about 5 to about 98 weight %, preferably about 20 to about 95 weight %, more preferably about 40 to about 95 weight %, and to the active ingredient in the composition is about 0.01 to about 15000 times by weight, preferably about 0.1 to about 1000 times by weight, and for still better result, about 0.1 to about 100 times by weight.

The above-mentioned polyglycerol fatty acid ester and lipid may be used as a mixture. For example, the combination of a polyglycerol fatty acid ester with a wax or the combination of a polyglycerol fatty acid ester with a hydrogenated oil can be mentioned. Specifically, a mixture of 2, 3 or more members selected from among behenic acid hexa(tetra)glyceride, stearic acid penta(tetra)glyceride, stearic acid penta(hexa)glyceride, polyglycerol polyricinolate (e.g. tetraglycerol polyricinolate, etc.), carnauba wax, hydrogenated castor oil, and microcrystalline wax, can be mentioned.

When the gastrointestinal mucosa-adhesive matrix comprising a viscogenic agent in addition to said polyglycerol fatty acid ester and/or lipid is used for the composition of the invention, the total amount of the polyglycerol fatty acid ester and lipid relative to the total weight of the composition is generally about 5 to about 98 weight %, preferably about 20 to about 95 weight %, more preferably about 40 to about 95 weight %, and to the active ingredient in the composition is about 0.01 to about 15000 times by weight, preferably about 0.1 to about 1000 times by weight, and for still better result, about 0.1 to about 100 times by weight.

A lipid may be incorporated in a matrix comprising the polyglycerol fatty acid ester. The lipid is a pharmaceutically acceptable water-insoluble substance capable of regulating the dissolution kinetics of the active ingredient. The lipid includes those species mentioned hereinbefore.

When a lipid and a polyglycerol fatty acid ester are used in combination, the amounts of the lipid and polyglycerol fatty acid need only be within the range not detracting from the adhesion to the gastrointestinal mucosa and can be selected from said range of total amount, and the amount of the lipid relative to the polyglycerol fatty acid ester may be about 0.01 to about 1000 times by weight, preferably about 0.1 to about 200 times by weight, and for still better results, about 0.1 to about 100 times by weight.

The active ingredient for use in the present invention may be absorbed from gastrointestinal mucosa or express its efficacy directly or indirectly in the gastrointestine, such as any anti-HP substance showing activity against strains of microorganism belonging to the genus Helicobacter (particularly *Helicobacter pylori*) whether directly or indirectly, thus including antimicrobial substance and inhibitors of urease which is known to be indispensable for survival of bacteria of the genus Helicobacter.

The antimicrobial substance includes but is not limited to antibiotics in the penicillin series (e.g. amoxicillin, benzylpenicillin, piperacillin, mecillinam, etc.), antibiotics in the cephalosporin series, macrolide antibiotics (e.g. erythromycin, clarithromycin, roxithromycin, azithromycin, etc.), tetracyclines (e.g. tetracycline, minocycline, etc.), aminoglycosides (e.g. gentamicin, amikacin, streptomycin, etc.), bismuth salts (e.g. bismuth acetate, bismuth citrate, bismuth salicylate, etc.), imidazoles (e.g. metronidazole, tinidazole, miconazole, etc.), quinolones (e.g. ofloxacin, ciprofloxacin, etc.), and tryptophanyl-t-RNA synthesis inhibitors (e.g. oxazolone derivatives (Preferably indolmycin) etc.). Particularly preferred are penicillins, macrolides, imidazoles, and tryptophanyl-t-RNA synthesis inhibitors. In particular a substance, such as amoxicillin, clarithromycin or indolmycin is preferred.

The urease inhibitor includes but is not limited to hydroxamic acid derivatives (e.g. acetohydroxamic acid and the compounds described or referred to in the above-mentioned Synopsis of Lectures at the 4th Annual Meeting of Medical Chemistry Group), phosphoramide derivatives [e.g. flurofamide (Micro. Ecol. Health Dis. referred to hereinbefore) and phenylphosphorodiamidate compound A (compound of Reference Example 2)], phosphates, thiols (e.g. 2-mercaptoethanol etc.), boric acid, halogen compounds (e.g. fluorides etc.), and cassia bark extract (the above-mentioned Synopsis of Lectures at the 117th Congress of Pharmaceutical Society of Japan).

The swelling material used in the present invention is a material which swells a viscogenic agent or accelerates the swell of a viscogenic agent caused by water.

Any type of swelling material can be used in the present invention as long as it has the characteristics described above and is pharmaceutically acceptable. For instance, preferably a curdlan and/or a low-substituted hydroxypropylcellulose can be used.

The amount of the swelling material in the gastrointestinal mucosa-adhesive composition of the present invention is about 0.5 to about 50 weight %, preferably about 1 to about 40 weight %, and for still better results, about 1 to about 30 weight %, relative to the total weight of the composition.

The curdlan for use in the present invention is a linear water-insoluble polysaccharide ($\beta$-1,3-glucan) produced by microorganisms (such as *Alcaligenes faecalis* var. *myxogenes* etc.), which includes such species as curdlan 10C3K, 13140, 12607, 12665, 13127, 13256, 13259, and 13660 [New Food Industry, 20, No. 10, p. 49 (1978)]. Among those and other species of curdlan, those which are acceptable as pharmaceutical bases or excipients can be employed. A preferred example is curdlan N (a food additive).

The amount of the curdlan in the gastrointestinal mucosa-adhesive composition of the invention relative to the total weight of the composition is about 0.5 to about 50 weight %, preferably about 1 to about 40 weight %, and more preferably about 1 to about 30 weight %.

The low-substituted hydroxypropylcellulose for use in the present invention is a cellulose derivative available upon substitution of hydroxypropoxy for some of the hydroxy groups of cellulose, which has a hydroxypropoxy content of 5.0 to 16.0% (as specified in the Japanese Pharmacopoeia Twelfth Edition). The low-substituted hydroxypropyl cellulose mentioned above is useful, in particular, one which has a hydroxypropoxy content of 7.0 to 13.0% (e.g. L-HPC™, Shin-Etsu Chemicals., Co., Ltd. is preferred. Thus, those derivatives with a degree of substitution within the above range and varying in particle diameter, such as LH-11™ (Shin-Etsu Chemicals., Co., Ltd.) hydroxypropoxy content 10.0 to 12.9%, particle size distribution $\geq$98% under 150 $\mu$m sieve and $\leq$0.5% on 180 $\mu$m sieve), LH-20™ (hydroxypropoxy content 13.0–16.0%, particle size distribution >90% under 75 $\mu$m sieve and $\leq$1.0% on 106 $\mu$m sieve), LH-21 (Shin-Etsu Chemicals., Co., Ltd., hydroxypropoxy content 10.0 to 12.9%, particle size distribution $\geq$90% under 75 $\mu$m sieve and $\leq$1.0% on 106 $\mu$m sieve), LH-22 (Shin-Etsu Chemicals., Co., Ltd., hydroxypropoxy content 7.0 to 9.9%, particle size distribution $\geq$90% under 75 $\mu$m sieve and $\leq$1.0% on 106 $\mu$m sieve), and LH-31

(Shin-Etsu Chemicals., Co., Ltd., hydroxypropoxy content 10.0 to 12.9%, mean particle diameter not greater than 30 μm, particle size distribution ≧50% under 45 μm sieve and ≦5.0% on 75 μm sieve), among others, can be utilized.

Preferably, LH-22 or LH-31 are utilized.

The amount of the low-substituted hydroxypropylcellulose in the gastrointestinal mucosa-adherent composition of the present invention is about 0.5 to about 50 weight %, preferably about 1 to about 40 weight %, and for still better results, about 1 to about 30 weight %, relative to the total weight of the composition.

Any type of viscogenic agent can be used in the present invention as long as it becomes sufficiently viscous with water to attach itself to the gastrointestinal mucosa and is pharmaceutically acceptable. Preferred, however, are those substances which are markedly swollen by water and develop high degrees of viscosity. The viscogenic agent, thus, includes synthetic polymers and naturally-occurring viscogenic materials.

The preferred synthetic polymer is a polymer such that the viscosity of a 2% aqueous solution thereof at 20° C. is about 3 to about 50000 cps., preferably about 10 to about 30000 cps., and for still better results, about 15 to about 30000 cps. However, when a basic or an acidic polymer which gains in viscosity on neutralization is used, the preferred polymer is such that the viscosity of a 0.2% solution thereof after neutralization at 20° C. is about 100 to about 500000 cps, preferably about 100 to about 200000 cps, and for still better results, about 1500 to about 100000 cps.

The value of the viscosity is measured with a Brookfield viscometer.

Preferably the above-mentioned polymer is an acidic polymer which includes but is not limited to carboxyl- or sulfo-containing polymers and the corresponding salt-containing polymers. Particularly preferred are carboxyl-containing polymers and carboxylate salt-containing polymers.

The carboxyl (inclusive of its salt)-containing polymer is preferably an acrylic homopolymer or copolymer containing acrylic acid as a monomer unit or a salt thereof. The salt includes monovalent metal salts such as the sodium salt, potassium salt, etc. and divalent metal salts such as the magnesium salt, calcium salt, ammonium salt, etc.

The acrylic polymer, inclusive of its salt, includes polymers containing carboxyl groups in a proportion of about 58 to about 63 weight % and having a molecular weight of about $20 \times 10^4$ to about $600 \times 10^4$, preferably about $100 \times 10^4$ to about $600 \times 10^4$, and more preferably about $100 \times 10^4$ to about $500 \times 10^4$. The preferred acrylic polymer, inclusive of its salt, includes acrylic acid homopolymers and their salts. Such polymers are listed under the heading of carboxyvinyl polymer in Japanese Standards of Pharmaceutical Ingredients (October 1986).

As specific examples of said acrylic polymer, there can be mentioned carbomer [Carbopol™ (hereinafter referred to as Carbopol), The B. F. Goodrich Company] 940, 934, 934P, 941, 1342, 974P, 971P (NF XVIII), EX214 etc., HIVISWAKO™ 103, 104, 105, and 204 (Wako Pure Chemical Industries), NOVEON AA1™ (The B. F. Goodrich Company), and calcium polycarbophil (USP XXIII)).

The naturally-occurring viscogenic agent includes but is not limited to mucin, agar, gelatin, pectin, carrageenin, sodium alginate, locust bean gum, xanthan gum, tragacanth gum, chitosan, pullulan, waxy starch, sucralfate, curdlan, and cellulose and its derivatives (cellulose sulfate and preferably hydroxypropylcellulose or hydroxypropylmethylcellulose).

The most preferred viscogenic agent is an acrylic polymer or its salt.

Those viscogenic agents can be used alone or in combination.

Referring to the amount of the viscogenic agent for use in the composition of the invention, its amount in the gastrointestinal mucosa-adherent matrix may for example be about 0.005 to about 99 weight %, preferably about 0.5 to about 45 weight %, more preferably about 1 to about 30 weight %, furthermore preferably about 1 to about 25 weight %, and for still better result, about 1 to about 20 weight %. When, for example, the viscogenic agent is dispersed in a matrix comprising the polyglycerol fatty acid ester and/or lipid, the amount of the viscogenic agent is about 0.005 to about 95 weight %, preferably about 0.5 to about 30 weight %, and more preferably about 1 to about 25 weight %, and for still better result, about 1 to about 20 weight % based on the total weight. When the matrix is coated with the viscogenic agent, the proportion of the viscogenic agent is also about 0.005 to about 95 weight %, preferably about 0.5 to about 30 weight %, and more preferably about 1 to about 25 weight %, and for still better result, about 1 to about 20 weight % based on the total weight.

When the composition of the present invention contains a curdlan as a swelling material, the composition is capable of attaching itself to the gastrointestinal mucosa even without addition of said viscogenic agent, for the curdlan acts as a viscogenic agent by itself. In this case, the curdlan may be formulated in an amount beyond the range defined hereinbefore for imparting the necessary adherent effect.

The gastrointestinal mucosa-adherent composition comprising the viscogenic agent dispersed in a matrix comprising a polyglycerol fatty acid ester and/or lipid may be any dispersion of the polyglycerol fatty acid ester and/or lipid, viscogenic agent, curdlan and/or low-substituted hydroxypropylcellulose, and active ingredient. Dispersion can be effected by the analogue to the per se known technology.

The technology for production of a gastrointestinal mucosa-adherent composition is now described.

1) The gastrointestinal mucosa-adherent composition, which is solid at atmospheric temperature, can be produced in a similar manner to the per se known technology. A typical process comprises melting the polyglycerol fatty acid ester and/or lipid at a temperature beyond its melting points adding said viscogenic agent, anti-HP agent, and curdlan and/or low-substituted hydroxypropylcellulose either at one time or serially to the melt to thereby disperse them in the melt, and cooling the dispersion. The heating temperature may for example be about 40 to about 150° C., preferably about 50 to about 110° C., and more preferably about 50 to about 100° C. This process can be carried out with a conventional granulating machine and the composition is preferably molded into solid beads (e.g. granules, finegranules, etc.) by spray cooling, for example spray chilling.

The spray chilling method may typically comprise dripping a mixed dispersion of the viscogenic agent, curdlan and/or low-substituted hydroxypropylcellulose, and active ingredient in a molten polyglycerol fatty acid ester and/or lipid at a constant flow rate onto a rotary disk revolving at a high speed of, for example, about 10 to about 6000 rpm, preferably about 900 to about 6000 rpm, and more preferably about 1000 to about 5000 rpm. The rotary disk may for example be a flat, smooth disk, typically made of aluminum and measuring about 5 to about 100 cm in diameter, preferably about 10 to about 20 cm in diameter. The dripping rate of said molten dispersion can be selected according to the designed particle diameter and is generally about 1 to about 1000 g/min., preferably about 2 to about 200 g/min., more preferably about 5 to about 100 g/min. The granules thus obtained are true to spheres so that a uniform film can be formed on their surface with good efficiency in the subsequent coating step.

An alternative production process comprises kneading the viscogenic agent, curdlan and/or low-substituted hydroxypropylcellulose, and active ingredient into the polyglycerol fatty acid ester and/or lipid and granulating the resulting dispersion. The solvent for use in this process may be a solvent of the common variety (e.g. methanol, acetonitrile, chloroform, etc.).

A further alternative process for producing the solid composition comprises the use of the melt granulation technology. A typical melt granulation process comprises heating the polyglycerol fatty acid-ester and/or lipid at a temperature near its melting point, for example, a temperature from its melting point to a temperature about 5° C. below the melting point, subjecting the resulting melt to granulation, such as the above-mentioned spray chilling, and suspending the resulting fine particles together with the viscogenic agent, anti-HP agent, and curdlan and/or low-substituted hydroxypropylcellulose under heating at a suitable temperature to provide an adherent matrix-drug system., In this case, the influence of heat on the active ingredient can be avoided. Therefore, even when the active ingredient is a peptide or a protein, a solid composition can be manufactured without deactivating of the active substance.

The solid composition comprising a matrix made up of a polyglycerol fatty acid ester and/or a lipid and coated with a viscogenic agent may be a preparation coated with such a viscogenic agent alone or a mixture of a viscogenic agent and a swelling material (e.g. curdlan and/or a low-substituted hydroxypropylcellulose etc), preferably with a coating material containing either a viscogenic agent alone or a viscogenic agent plus a curdlan and/or a low-substituted hydroxypropylcellulose. The coating material may be a composition containing at least one member selected from among said polyglycerol fatty acid ester, said lipid, and said water-insoluble polymer. When a viscogenic agent which is sparingly compatible or incompatible with the components of the solid composition is employed for coating, the solid composition can be provided with a film in which the viscogenic agent has been dispersed. The coating material may further contain the additives mentioned hereinbefore.

The water-insoluble (hydrophobic) polymer includes but is not limited to hydroxypropylmethylcellulose phthalate (The Japanese Pharmacopoeia Twelfth Edition), hydroxypropylmethylcellulose acetate succinate (Shin-Etsu Chemicals Co., Ltd.), carboxymethylethylcellulose (Freund Industries Co., Ltd., CMEC, Japanese Standards of Pharmaceutical Ingredients, 1986), cellulose acetate trimellitate (Eastman), cellulose acetate phthalate (The Japanese Pharmacopoeia Twelfth Edition), ethylcellulose (Asahi Chemical Industry Co., Ltd.), aminoalkyl methacrylate copolymer (Röhm-Pharma, Eudragit™ RS-100, RL-100, RL-PO, RS-PO, RS-30D, RL-30D), methacrylic acid-ethyl acrylate copolymer (Röhm-Pharma, Eudragit™ L100-55), methacrylic acid-methyl methacrylate copolymer (Röhm-Pharma, Eudragit™ L-100, S-100), Eudragit™ 30D-55, Eudragit™ NE-30D (Röhm-Pharma), and polyvinyl acetate (Colorcon). Those hydrophobic polymers can be used independently or as a mixture of two or more different polymers.

The proportion of the viscogenic agent in the coating material is about 0.005 to about 100 weight %, preferably about 0.05 to about 95 weight %, more preferably about 0.05 to about 30 weight %, and for still better result, about 1 to about 10 weight % based on the whole solid fraction of the coating material.

When at least one of the polyglycerol fatty acid ester, lipid, and hydrophobic polymer is used in combination with the viscogenic agent for the coating material, the proportion of the viscogenic agent based on the total weight of the solid fraction of the coating material is about 0.05 to about 95 weight %, preferably about 0.5 to about 95 weight %, more preferably about 0.5 to about 30 weight %, futhermore preferably about 5 to about 30 weight %, and for still better result, about 5 to about 25 weight %.

Referring further to the coating material, two or more members selected from the class consisting of the polyglycerol fatty acid ester, lipid, and hydrophobic polymer can be used in combination. In this case, based on each part by weight of the whole polyglycerol fatty acid ester and/or lipid, the remaining component is used in a proportion of about 0.0001 to about 1000 part by weight, preferably about 0.01 to about 100 part by weight, and more preferably about 0.01 to about 10 part by weight.

The coating amount can be selected according to the type of solid composition and the desired strength of adhesion to the mucosa. For example, the coating amount for a solid composition may be about 0.1 to about 30 weight %, preferably about 0.5 to about 20 weight %, for tablets and about 0.1 to about 100 weight %, preferably about 1 to about 50 weight %, for fine granules.

Where necessary, the coating material may be supplemented with the common additives such as those mentioned hereinbefore. For example, the coating material and the additive may be added together or separately, etc. applied. The proportion of the additive relative to the solid fraction of the coating material is about 0.1 to about 70 weight %, preferably about 1 to about 50 weight %, and more preferably about 20 to about 50 weight %.

The coating technology that can be used includes a variety of per se known methods, such as pan coating, fluidized-bed coating, roll coating, and so on. When the coating material is a solution or dispersion containing water or an organic solvent, the spray coating method can also be employed. There is no particular limitation on the kind of said water or organic solvent. Thus, for example, alcohols such as methanol, ethanol, isopropyl alcohol, etc.; ketones such as acetone etc.; and halogenated hydrocarbons such as chloroform, dichloromethane, trichloromethane, etc. can be used.

When the polyglycerol fatty acid ester and/or lipid is used for coating, the objective coated composition can be produced by melting the polyglycerol fatty acid ester and/or lipid, optionally together with other additives, under heating, emulsifying the melt with water, spray-coating the surface of a solid composition with the resulting emulsion, and drying the coat. An alternative procedure comprises adding the coating material to the solid composition preheated in a coating pan or the like and melt-spreading the coating.

The solid composition is coated generally at a temperature of about 25 to about 60° C. and preferably at about 25 to about 40° C.

The coating time can be judiciously selected with reference to the coating method, the characteristics and amount of the coating material, and characteristics of the substrate solid composition.

Insofar as a sufficient adhesion to the gastrointestinal mucosa can be assured, the gastrointestinal mucosa-adherent solid composition may, if necessary, be further coated with a conventional gastric coating agent or a water-soluble coating agent.

The gastrointestinal mucosa-adherent composition according to the present invention can generally be administered orally as it is or in a suitable preparation. The solid oral dosage form includes but is not limited to fine granules, granules, pills, tablets manufactured by compressing said fine granules or granules with a tablet machine, and capsules manufactured by filling said fine granules or granules into suitable capsule shells. Among those preparations, fine granules and granules are preferred.

The particle size distribution of said fine granules may for example be: particles measuring about 10 to about 500 μm in diameter accounting for not less than about 75 weight %, particles larger than about 500 μm accounting for not more than about 5 weight %, and particles smaller than about 10 μm accounting for not more than about 10 weight %. The preferred distribution is about 105 to about 500 μm accounting for about ≧75 weight %, about ≧500 μm accounting for not more than about 5 weight %, and about ≦74 μm accounting for not more than about 10 weight %. The particle size distribution of said granules may for example be about 500 to about 1410 μm accounting for not less than about 90 weight % and about ≦177 μm accounting for not more than about 5 weight %.

2). When the gastrointestinal mucosa-adherent composition is to be provided as a liquid composition, such a liquid composition can be manufactured by the manner similar to the per se known technology. A typical procedure comprises mixing a polyglycerol fatty acid ester and/or a lipid, which is liquid at atmospheric temperature, a viscogenic agent, a active ingredient, and a swelling material (e.g. a curdlan and/or a low-substituted hydroxypropylcellulose etc.) all at once or serially to provide a dispersion or solution.

The dosage form comprising such a liquid adherent mucosal medication system includes but is not limited to syrups, emulsions, suspensions, and encapsulated versions thereof.

The proportion of the active ingredient (e.g. an anti-HP agent etc.) in the composition of the invention is about 0.005 to about 95 weight %, preferably about 1 to about 95 weight %, and more preferably about 10 to about 95 weight %, and for still better result, about 10 to about 50.

The composition of the present invention is relatively non-toxic, and effective, for instance, in the treatment of *Helicobacter pylori*-harboring mammals (e.g. feline, bovine, canine, equine, goat, monkey, human, etc.). The composition exhibits marked efficacy in the clearance and extermination of *Helicobacter pylori* in such animals. Therefore the composition is useful for the prophylaxis, treatment, and prevention of relapse of *Helicobacter pylori* related gastrointestinal disease. The indication includes but is not limited to gastritis and gastrointestinal ulcer, and stomach cancer, and a particularly remarkable response can be obtained in the treatment of gastrointestinal ulcer.

The gastrointestinal mucosa-adherent composition of the present invention can be administered, generally by the oral route, to mammals including humans. If desired, the composition may be compounded or formulated with pharmacologically and pharmaceutically acceptable additives (e.g. diluent, excipient, binder, disintegrator, coloring agent, stabilizer, etc.) just as mentioned hereinbefore.

The preparations containing the gastrointestinal mucosa-adherent composition may be further supplemented with other pharmacologically active ingredients, such as antimicrobials, antiulcerative agents, antacids, gastric acid antisecretory agents, analgesics, and nutrients (vitamins etc.), unless the pharmacologic activities of the respective ingredients are compromised by mutual interference.

The antibacterials mentioned above include but are not limited to macrolides (e.g. clarithromycin, roxithromycin, azithromycin, etc.), quinolones (e.g. tarivid, ozex, pefloxacin, etc.), penicillins (e.g. furopenem etc.), and cephalosporins (e.g. flumax etc.).

The antiulcerative agent includes but is not limited to therapeutic drugs for gastrointestinal ulcer, such as proton pump inhibitors, $H_2$ blockers, and mucosal protectant antiulceratives.

The proton pump inhibitor includes benzimidazole compounds having antiulcerative activity, particularly 2-[(pyridyl)-methylsulfinyl or methylthio]benzimidazole derivatives and their salts. Specifically, 2-[[3-methyl-4-(2, 2,2-trifluoroethoxy)-2-pyridinyl]methylsulfinyl]-1H-benzimidazole (lansoprazole), 2-[(2-pyridinylmethyl) sulfinyl]-1H-benzimidazole (timoprazole), 5-methoxy-2-[[(4-methoxy-3,5-dimethyl-2-pyridinyl)methyl]sulfinyl]-1H-benzimidazole (omeprazole), 2-[2-[4-(3-methoxypropoxy)-3-methylpyridyl]methylsulfinyl]-1H-benzimidazole sodium, 5-(difluoromethoxy)-2-[[(3,4-dimethoxy-2-pyridinyl)methyl]sulfinyl]-1H-benzimidazole (pantoprazole), etc. can be mentioned. The above benzimidazole compounds and salts can be produced by the processes described in, inter alia, Japanese Patent Unexamined Publication NO.141783/1979, Patent Unexamined Publication NO.192880/1983, Patent Unexamined Publication NO.50978/1986, Patent Unexamined Publication NO.116576/1987 and Patent Unexamined Publication NO.59043/1993 or any production processes analogous thereto. Aside from the above compounds, 2-[[o-(isobutylamino)benzyl]sulfinyl]benzimidazole (leminoprazole) and 2-[4-methoxy-6,7,8,9-tetrahydro-5H-cyclohepta[b]pyridine can also be mentioned.

The $H_2$ blocker includes but is not limited to 2-cyano-1-methyl-3-[2-[[(5-methylimidazol-4-yl)methyl]thio]ethyl] guanidine (cimetidine), N-[2-[[[5-[(dimethylamino)methyl] furanyl]thio]ethyl]-N'-methyl-2-nitro-1,1-ethenediamine (ranitidine), and (±)-2-(furfurylsulfinyl)-N-[4-[4-(piperidinylmethyl)-2-pyridyl]oxy(z)-2-butinyl]acetamide (loctidine).

The mucosal protectant antiulcerative includes but is not limited to (z)-7-[(1R,2R,3R)-2-[(E)-(3R)-3-hydroxy-4,4-dimethyl-1-octenyl]-3-methyl-5-oxocyclopentyl]-5-heptenoic acid (trimoprostil, ulstar), 1-butyric acid-7-(L-2-aminobutyric acid-26-L-aspartic acid-27-L-valine-29-L-alanine)calcitonin (elcatonin), and sodium 3-ethyl-7-isopropyl-1-azulenesulfonate (egualen sodium).

When the above composition is processed into a solid preparation, those additives which are conventionally used in the manufacture of solid pharmaceutical preparations (e.g. tablets, fine granules, granules, etc.) can be employed. Among such additives are excipients such as corn starch, talc, crystalline cellulose (Avicel), powdered sucrose, magnesium stearate, mannitol, light silicic anhydride, magnesium carbonate, calcium carbonate, L-cysteine, etc.; binders such as starch, sucrose, gelatin, gum arabic powder, methylcellulose, carboxymethylcellulose, carboxymethylcellulose sodium, hydroxypropylcellulose, hydroxypropylmethylcellulose, polyvinylpyrrolidone, pullulan, dextrin, etc.; disintegrators such as carboxymethylcellulose calcium, low-substituted hydroxypropylmethylcellulose, croscarmellose sodium, etc.; anionic surfactants such as sodium alkyl sulfonates etc. and nonionic surfactants such as polyoxyethylene sorbitan fatty acid esters, polyoxyethylene fatty acid esters, polyoxyethylated castor oil derivatives, etc.; antacids or mucosal protectants such as magnesium hydroxide, magnesium aluminosilicate, sucralfate, etc.; coloring agents; corrigents; adsorbents; antiseptics; lubricants; and antistatic agents. The levels of addition of those additives can be selected within the range not detracting from adhesion to the mucosa.

The dosage of the composition of the invention should vary with different dosage forms, administration modalities, and included active ingredient. It is likely that compared with administration of the ingredient alone, the dosage of the drug can be reduced to one-half through about one-twentieth when the composition of the invention is used.

When the pharmaceutical composition of the invention is to be administered orally to a human being for the therapy of *Helicobacter pylori* infection, taking the case in which the active ingredient is an antimicrobial substance as an example, the daily dose for an adult patient may be about 0.1 to about 50 mg/kg or preferably about 0.3 to about 40 mg/kg in terms of the active substance. Taking the case in which the active substance is a urease inhibitor as an example, the daily dose for an adult patient is about 0.05 to about 100 mg/kg or preferably about 0.2 to about 100 mg/kg, more preferably about 0.2 to about 20 mg/kg, furthermore preferably about 0.2 to about 10 mg/kg, and for still better result, about 0.5 to about 10 mg/kg in terms of the active substance.

Furthermore, the preparation of the invention and an independent dosage form comprising said antiulcerative agent can be administered to the same recipient either concurrently or at staggered times for the treatment of gastritis or gastrointestinal ulcer and such a combination therapy is useful for the therapy or symptomatic relief of such diseases.

MODE OF WORKING THE INVENTION

The following examples and test examples illustrate the present invention in further detail, however those examples should by no means be construed as limiting the scope of the invention.

Reference Example 1

5-Methyl-2-thiophenecarboxamide

5-Methyl-2-thiophenecarbaldehyde (2.6 g, 0.1 M), hydroxylamine hydrochloride (8.3 g, 0.12 M), and sodium acetate (9.8 g, 0.12 M) were added to. acetic acid (50 ml) and the mixture was refluxed for 13 to 15 hours. After disappearance of the starting material was confirmed by high performance liquid chromatography (HPLC retention time ca 13 min.), the reaction mixture was concentrated under reduced pressure to about one-half of its volume. To this concentrate was added concentrated hydrochloric acid (100 ml) and the reaction was allowed to proceed at 60° C. for 4 hours. The reaction mixture was then diluted with 100 ml of water and stirred under ice-cooling for 30 minutes. The resulting crystals were recovered by filtration and rinsed with 100 ml of iced water to provide 5-methyl-2-thiophenecarboxamide (HPLC retention time ca 4 min.) (11.6 g, yield 82%).

HPLC parameter settings

Column: GL Sciences' Inertsil ODS-3, 5 m, 4.6×150 mm

Eluent: acetonitrile: 0.05 M potassium dihydrogen phosphate (aq. sol.)=30:70

Detection wavelength: 231 nm

Flow rate: 1.0 ml/min.

$^1$H-NMR (DMSO-$d_6$) d: 2.54 (3H, d, $CH_3$), 7.01 (1H, dd, thiophen-4-H), 7.78 (1H, dd, thiophen-3-H).

Reference Example 2

N-(diaminophosphinyl)-5-methyl-2-thiophenecarboxamide

5-Methyl-2-thiophenecarboxamide (7.6 g, 47 mM) was suspended in toluene (50 ml), followed by addition of phosphorus pentachloride (10.9 g, 50 mM) with vigorous stirring at room temperature. The mixture was heated to 65° C. and stirred at that temperature for 30 minutes. Then, under cooling with ice, formic acid (2.0 ml) was added dropwise. The mixture was stirred at 25° C. for 30 minutes, after which the toluene was distilled off under reduced pressure. After the residue was dissolved tetrahydrofuran (THF, 100 ml), 25% aqueous ammonia (17.1 ml) was added with ice-cooling and the mixture was stirred at 25° C. for 30 minutes. Then, toluene (100 ml) was added and the crystals that separated out were harvested by filtration. This crystal crop was rinsed with THF (50 ml) and water (50 ml) and dried in vacuo to provide N-(diaminophosphinyl)-5-methyl-2-thiophenecarboxamide (6.78 g, 64%). m.p. 285–297° C. (decomp.).

EXAMPLE 1

Production of a urease inhibitor-containing gastrointestinal mucosa-adherent preparation A mixture of hydrogenated caster oil (Lubri wax 101™, Freund Industrial Co. Ltd.) (63.0 g) and behenic acid hexa (tetra) glyceride (HB-310™, Sakamoto Yakuhin Kogyo Co. Ltd.)(5.0 g) was melted at 84° C. To this melt, 4.0 g of N-(diaminophosphinyl)-5-methyl-2-thiophenecarboxamide (hereinafter referred to as compound A), 8.0 g of acrylic polymer (HIVISWAKO 104™, Wako Pure Chemical Industries, Ltd.) and 20.0 g of Curdlan (Takeda Chemical Industries, Ltd.) were serially added and the mixture was stirred for dispersion at a constant temperature of 84° C. for 15 minutes. This molten mixture was dropped onto a 15 cm (di.) aluminum disk rotating at 1950 rpm at a flow rate of 10 g/min, whereby spherical fine granules passing through a 42-mesh sieve but failing to pass through a 60-mesh sieve (hereinafter referred to briefly as 42/60 mesh) were obtained.

EXAMPLE 2

Production of a urease inhibitor-containing gastrointestinal mucosa-adherent preparation A mixture of hydrogenated caster oil (Lubri wax 101™, Freund Industrial Co. Ltd.) (63.0 g) and behenic acid hexa (tetra) glyceride, (HB-310™, Sakamoto Yakuhin Kogyo Co. Ltd.)(5.0 g) was melted at 84° C. To this melt, 4.0 g of compound A, 8.0 g of acrylic polymer (HIVISWAKO 104™, Wako Pure Chemical Industries, Ltd.) and 20.0 g of low substituted hydroxypropylcellulose (LH-31™, Shin-Etsu Chemicals) were serially added and the mixture was stirred for dispersion at a constant temperature of 84° C. for 15 minutes. This molten mixture was dropped onto a 15 cm (di.) aluminum disk rotating at 1950 rpm at a flow rate of 10 g/min, whereby 42/60 mesh spherical fine granules were obtained.

EXAMPLE 3

Production of a urease inhibitor-containing gastrointestinal mucosa-adherent preparation Behenic acid hexa (tetra) glyceride (HB-310™, Sakamoto Yakuhin Kogyo Co. Ltd.)(81.5 g) was melted at 84° C. To this melt, 0.5 g of compound A, 8.0 g of acrylic polymer (HIVISWAKO 104™, Wako Pure Chemical Industries, Ltd.) and 10.0 g of Curdlan (Takeda Chemical Industries, Ltd.) were serially added and the mixture was stirred for dispersion at a constant temperature of 84° C. for 15 minutes. This molten mixture was dropped onto a 15 cm (di.) aluminum disk rotating at 1950 rpm at a flow rate of 10 g/min, whereby 42/60 mesh spherical fine granules were obtained.

EXAMPLE 4

Production of a urease inhibitor-containing gastrointestinal mucosa-adherent preparation A mixture of hydrogenated caster oil (Lubri wax 101™, Freund Industrial Co. Ltd.) (54.0 g) and behenic acid hexa (tetra) glyceride (HB-310™, Sakamoto Yakuhin Kogyo Co. Ltd.)(1.0 g) was melted at 84° C. To this melt, 35.0 g of compound A, 5.0 g of acrylic polymer (HIVISWAKO 104™, Wako Pure Chemical Industries, Ltd.) and 5.0 g of Curdlan (Takeda Chemical Industries, Ltd.) were serially added and the mixture was stirred for dispersion at a constant temperature of 84° C. for 15 minutes. This molten mixture was dropped onto a 15 cm (di.) aluminum disk rotating at 1950 rpm at a flow rate of 10 g/min, whereby 42/60 mesh spherical fine granules were obtained.

EXAMPLE 5

Production of a urease inhibitor-containing gastrointestinal mucosa-adherent preparation A mixture of hydrogenated caster oil (Lubri wax 101™, Freund Industrial Co. Ltd.) (35.0 g) and behenic acid hexa (tetra) glyceride (HB-310™, Sakamoto Yakuhin Kogyo Co. Ltd.)(1.0 g) was melted at 84° C. To this melt, 35.0 g of compound A, 5.0 g of acrylic polymer (HIVISWAKO 104™ Wako Pure Chemical Industries, Ltd.) and 5.0 g of low substituted hydroxypropylcellulose (LH-31™, Shin-Etsu Chemicals) were serially added and the mixture was stirred for dispersion at a constant temperature of 84° C. for 15 minutes. This molten mixture was dropped onto a 15 cm (di.) aluminum disk rotating at 1950 rpm at a flow rate of 10 g/min, whereby 42/60 mesh spherical fine granules were obtained.

EXAMPLE 6

Production of a urease inhibitor-containing gastrointestinal mucosa-adherent preparation A mixture of hydrogenated caster oil (Lubri wax 101™, Freund Industrial Co. Ltd.) (54.0 g) and behenic acid hexa (tetra) glyceride (HB-310™, Sakamoto Yakuhin Kogyo Co. Ltd.)(1.0 g) was melted at 84° C. To this melt, 35.0 g of compound A, 5.0 g of acrylic polymer (HIVISWAKO 104™, Wako Pure Chemical,Industries, Ltd.) and 5.0 g of low substituted hydroxypropylcellulose (LH-31™, Shin-Etsu Chemicals) were serially added and the mixture was stirred for dispersion at a constant temperature of 84° C. for 15 minutes. This molten mixture was dropped onto a 15 cm (di.) aluminum disk rotating at 1950 rpm at a flow rate of 10 g/min, whereby 42/60 mesh spherical fine granules were obtained.

EXAMPLE 7

Production of a urease inhibitor-containing gastrointestinal mucosa-adherent preparation Hydrogenated caster oil (Lubri wax 101™, Freund Industrial Co. Ltd.) (76.0 g) was melted at 84° C. To this melt, 4.0 g of compound A, 10.0 g of acrylic polymer (HIVISWAKO 104™, Wako Pure Chemical Industries, Ltd.) and 10.0 g of low substituted hydroxypropylcellulose (LH-31™, Shin-Etsu Chemicals) were serially added and the mixture was stirred for dispersion at a constant temperature of 84° C. for 15 minutes. This molten mixture was dropped onto a 15 cm (di.) aluminum disk rotating at 1950 rpm at a flow rate of 10 g/min, whereby 42/60 mesh spherical fine granules were obtained.

Test Example 1

In vivo anti-*Helicobacter pylori* effect of the compound A-containing gastrointestinal mucosa-adherent preparation Mice (Crj: ICR) infected with *Helicobacter pylori* (hereinafter sometimes referred to briefly as HP) were subcutaneously dosed with a lansoprazole (hereinafter referred to briefly as LPZ)-containing 0.5% methylcellulose suspension. At 30 minutes after administration, the compound A-containing gastrointestinal mucosa-adherent preparation obtained in Example 6 (AdMMS in Table 1) or a 1.0% $NaHCO_3$/0.5% methylcellulose suspension containing compound A (Suspension in Table 1) was orally administered twice a day for 3 consecutive days at a dose of 10 mg/kg as compound A for AdMMS or 100 mg/kg as compound A for the suspension. At 16 hours after the final dose, the stomach was excised and the gastric wall was homogenized and serial dilutions were plated on the HP selective medium. The inoculated medium was incubated for 4 days at 37° C. under microaerobic conditions and the number of viable cells was counted. The results are shown in Table 1.

TABLE 1

| | Dose (mg/kg) | | Bacterial recovery Log CFU/gastric wall |
|---|---|---|---|
| Preparation | Compound-A | LPZ | Mean ± SE |
| Control | 0 | 0 | 4.54 ± 0.30 |
| Suspension | 100 | 10 | 3.14 ± 0.86 |
| AdMMS | 10 | 10 | 3.39 ± 1.21 |

The compound A-containing gastrointestinal mucosa-adherent preparation (AdMMS) showed an equivalent anti-HP effect at the dose of one-tenth of the suspension.

EXAMPLE 8

Production of amoxicillin-containing gastrointestinal mucosa-adherent preparation Hydrogenated caster oil (Lubri wax 101™, Freund Industrial Co. Ltd.) (75.0 g) was melted at 95° C. To this melt, 1.5 g of amoxicillin (Beecham Pharmaceuticals (PTE) Ltd.) (hereinafter referred to as AMPC), 10.0 g of acrylic polymer (HIVISWAKO 104™, Wako Pure Chemical Industries, Ltd.) and 13.5 g of Curdlan (Takeda Chemical Industries, Ltd.) were serially added and the mixture was stirred for dispersion at a constant temperature of 95° C. for 15 minutes. This molten mixture was dropped onto a 15 cm (di.) aluminum disk rotating at 1950 rpm at a flow rate of 10 g/min, whereby 42/60 mesh spherical fine granules were obtained.

Comparative Example 1

Production of amoxicillin-containing gastrointestinal mucosa-adherent preparation Carnauba wax (Polishing wax 103, Freund Industrial Co. Ltd.) (88.5 g) was melted at 95° C. To this melt, 1.5 g of ambxicillin (Beecham Pharmaceuticals (PTE) Ltd.) (hereinafter referred to as AMPC) and 10.0 g of acrylic polymer (HIVISWAKO 104™, Wako Pure Chemical Industries, Ltd.) were serially added and the mixture was stirred for dispersion at a constant temperature of 95° C. for 15 minutes. This molten mixture was dropped onto a 15 cm (di.) aluminum disk rotating at 1950 rpm at a flow rate of 10 g/min, whereby 42/60 mesh spherical fine granules were obtained.

Test Example 2

In vivo anti-*Helicobacter pylori* effect of the AMPC-containing gastrointestinal mucosa-adherent preparation Mongolian gerbils (MGS/Sea) infected with HP were orally dosed with the AMPC-containing gastrointestinal mucosa-adherent preparation obtained in Example 8 (AMPC-AdMMS-8 in Table 2), the AMPC-containing gastrointestinal mucosa-adherent preparation obtained in Comparative Example 1 (AMPC-AdMMS-C1 in Table 2), and a 0.5% methylcellulose suspension containing AMPC (AMPC suspension in Table 2), respectively at a dose of 10 mg/kg as AMPC twice a day for 3 consecutive days. At 16 hours after the final dose, the stomach was excised and the gastric wall was homogenized and serial dilutions were plated on the HP selective medium. The inoculated medium was incubated for 4 days at 37° C. under microaerobic conditions and the number of viable cells was counted. The results are shown in Table 2.

TABLE 2

| Formulation | Dose (mg/kg) AMPC | Clearance rate Cleared/tota l (%) | Bacterial recovery Log CFU/gastric wall Mean ± SE |
|---|---|---|---|
| Control | 0 | 0/5 (0) | 7.02 ± 0.33 |
| AMPC-suspension | 10 | 1/5 (20) | 3.12 ± 1.45 |
| AMPC-AdMMS-8 | 10 | 5/5 (100) | ND |
| AMPC-AdMMS-C1 | 10 | 2/5 (40) | 1.74 ± 0.38 |

ND means not detected.

Compared with the AMPC-suspension, both AMPC-containing gastrointestinal mucosa-adherent preparations showed higher anti-HP activity and, in particular, the AMPC-containing gastrointestinal mucosa-adherent preparation containing curdlan showed a remarkably superior effect.

EXAMPLE 9

Production of a urease inhibitor-containing gastrointestinal mucosa-adherent preparation Hydrogenated caster oil (Lubri wax 101™, Freund Industrial Co. Ltd.) (78.0 g) was melted at 84° C. To this melt, 4.0 g of compound-A, 8.0 g of acrylic polymer (HIVISWAKO 104™, Wako Pure Chemical Industries, Ltd.) and 10.0 g of Curdlan (Takeda Chemical Industries, Ltd.) were serially added and the mixture was stirred for dispersion at a constant temperature of 84° C. for 15 minutes. This molten mixture was dropped onto a 15 cm (di.) aluminum disk rotating at 1950 rpm at a flow rate of 10 g/min, whereby 42/60 mesh spherical fine granules were obtained.

EXAMPLE 10

Production of an indolmycin-containing gastrointestinal mucosa-adherent Preparation Behenic acid hexa (tetra) glyceride (HB-310™ Sakamoto Yakuhin Kogyo Co. Ltd.)(60.0 g) was melted at 80° C. To this melt, 30.0 g of indolmycin, 6.0 g of acrylic polymer (HIVISWAKO 104™, Wako Pure Chemical Industries, Ltd.) and 4.0 g of low substituted hydroxypropylcellulose (LH-31™, Shin-Etsu Chemicals) were serially added and the mixture was stirred for dispersion at a constant temperature of 80° C. for 2 hours. This molten mixture was dropped onto a 15 cm (di.) aluminum disk rotating at 3960 rpm at a flow rate of 50 g/min, whereby spherical fine granules passing through a 42-mesh (hereinafter referred to briefly as 42-mesh pass) were obtained.

EXAMPLE 11

Production of an indolmycin-containing gastrointestinal mucosa-adherent preparation Behenic acid hexa (tetra) glyceride (HB-310™, Sakamoto Yakuhin Kogyo Co. Ltd.)(55.0 g) was melted at 80° C. To this melt, 35.0 g of indolmycin, 6.0 g of acrylic polymer (HIVISWAKO 104™, Wako Pure Chemical Industries, Ltd.) and 4.0 g of low substituted hydroxypropylcellulose (LH-31™, Shin-Etsu Chemicals) were serially added and the mixture was stirred for dispersion at a constant temperature of 80° C. for 2 hours. This molten mixture was dropped onto a 15 cm (di.) aluminum disk rotating at 3960 rpm at a flow rate of 50 g/min, whereby 42-mesh pass spherical fine granules were obtained.

EXAMPLE 12

Production of an indolmycin-containing gastrointestinal mucosa-adherent preparation A mixture of hydrogenated castor oil (Lubri wax 101™, Freund Industrial Co. Ltd.) (40.0 g) and behenic acid hexa (tetra) glyceride (HB-310™, Sakamoto Yakuhin Kogyo Co. Ltd.)(30.0 g) was melted at 85° C. To this melt, 10.0 g of indolmycin, 10.0 g of acrylic polymer (HIVISWAKO 104™, Wako Pure Chemical Industries, Ltd.) and 10.0 g of low substituted hydroxypropylcellulose (LH-31™, Shin-Etsu Chemicals) were serially added and the mixture was stirred for dispersion at a constant temperature of 85° C. for 2 hours. This molten mixture was dropped onto a 15 cm (di.) aluminum disk rotating at 2700 rpm at a flow rate of 50 g/min, whereby 42/119-mesh pass spherical fine granules were obtained.

EXAMPLE 13

Production of an indolmycin-containing gastrointestinal mucosa-adherent preparation Behenic acid hexa (tetra) glyceride (HB-310™, Sakamoto Yakuhin Kogyo Co. Ltd.)(87.0 g) was melted at 80° C. To this melt, 1.0 g of indolmycin, 8.0 g of acrylic polymer (HIVISWAKO 104™, Wako Pure Chemical Industries, Ltd.) and 4.0 g of low substituted hydroxypropylcellulose (LH-31™, Shin-Etsu Chemicals) were serially added and the mixture was stirred for dispersion at a constant temperature of 80° C. for 2 hours. This molten mixture was dropped onto a 15 cm (di.) aluminum disk rotating at 2400 rpm at a flow rate of 50 g/min, whereby 42-mesh pass spherical fine granules were obtained.

EXAMPLE 14

Production of an indolmycin-containing qastrointestinal mucosa-adherent preparation Behenic acid hexa (tetra) glyceride (HB-310™, Sakamoto Yakuhin Kogyo Co. Ltd.) was melted at 80° C. This melt was dropped onto a 15 cm (di.) aluminum disk rotating at 1800 rpm at a flow rate of 50 g/min, whereby 42/119 mesh spherical fine granules were obtained. Indolmycin (250 g), acrylic polymer (HIVISWAKO 104™, Wako Pure Chemical Industries, Ltd.), (50 g) and low substituted hydroxypropylcellulose (LH-31™, Shin-Etsu Chemicals)(50 g) were mixed for 1 min in High Speed Mixer. To this mixture, 150 g of the fine granules were added and stirred at a constant temperature of 70° C. at 500 rpm, whereby 42-mesh pass spherical fine granules were obtained.

EXAMPLE 15

Production of an indolmycin-containing gastrointestinal mucosa-adherent preparation A mixture of behenic acid hexa (tetra) glyceride (HB-310™, Sakamoto Yakuhin Kogyo Co. Ltd.)(59.5 g) and ricinoleic acid poly (tetra) glyceride (CRS-75, Sakamoto Yakuhin Kogyo Co. Ltd.)(0.5 g) was melted at 80° C. To this melt, 30.0 g of indolmycin, 6.0 g of acrylic polymer (HIVISWAKO 104™, Wako Pure Chemical Industries, Ltd.) and 4.0 g of low substituted hydroxypropylcellulose (LH-31™, Shin-Etsu Chemicals) were serially added and the mixture was stirred for dispersion at a constant temperature of 80° C. for 2 hours. This molten mixture was dropped onto a 15 cm (di.) aluminum.disk rotating at 3960 rpm at a flow rate of 50 g/min, whereby 42-mesh pass spherical fine granules were obtained.

EXAMPLE 16

Production of an indolmycin-containing gastrointestinal mucosa-adherent preparation A mixture of hydrogenated caster oil (Lubri wax 101™, Freund Industrial Co. Ltd.) (40.0 g) and behenic acid hexa (tetra) glyceride (HB-310™, Sakamoto Yakuhin Kogyo Co. Ltd.)(30.0 g) was melted at 85° C. To this melt, 10.0 g of indolmycin, 10.0 g of acrylic polymer (HIVISWAKO 104™, Wako Pure Chemical Industries, Ltd.) and 10.0 g of low substituted hydroxypropylcellulose (LH-31™, Shin-Etsu Chemicals) were serially added and the mixture was stirred for dispersion at a constant temperature of 85° C. for 2 hours. This molten mixture was dropped onto a 15 cm (di.) aluminum disk rotating at 3960 rpm at a flow rate of 50 g/min, whereby 42/119-mesh spherical fine granules were obtained.

EXAMPLE 17

Production of an indolmycin-containing gastrointestinal mucosa-adherent preparation A mixture of hydrogenated caster oil (Lubri wax 101™, Freund Industrial Co. Ltd.) (40.0 g) and behenic acid hexa (tetra) glyceride (HB-310™, Sakamoto Yakuhin Kogyo Co. Ltd.)(30.0 g) was melted at 85° C. To this melt, 10.0 g of indolmycin, 10.0 g of acrylic polymer (HIVISWAKO 104™, Wako Pure Chemical Industries, Ltd.) and 10.0 g of low substituted hydroxypropylcellulose (LH-22, Shin-Etsu Chemicals) were serially added and the mixture was stirred for dispersion at a constant temperature of 85° C. for 2 hours. This molten mixture was dropped onto a 15 cm (di.) aluminum disk rotating at 3960 rpm at a flow rate of 50 g/min, whereby 42/119-mesh spherical fine granules were obtained.

EXAMPLE 18

Production of an indolmycin-containing gastrointestinal mucosa-adherent preparation A mixture of hydrogenated caster oil (Lubri wax 101™, Freund Industrial Co. Ltd.) (40.0 g) and behenic acid hexa (tetra) glyceride (HB-310™, Sakamoto Yakuhin Kogyo Co. Ltd.)(30.0 g) was melted at 85° C. To this melt, 10.0 g of indolmycin, 10.0 g of acrylic polymer (HIVISWAKO 104™, Wako Pure Chemical Industries, Ltd.) and 10.0 g of Curdlan (Takeda Chemical Industries, Ltd.) were serially added and the mixture was stirred for dispersion at a constant temperature of 85° C. for 2 hours. This molten mixture was dropped onto a 15 cm (di.) aluminum disk rotating at 3960 rpm at a flow rate of 50 g/min, whereby 42/119-mesh spherical fine granules were obtained.

Comparative Example 2

Production of an indolmycin-containing gastrointestinal mucosa-adherent preparation A mixture of hydrogenated caster oil (Lubri wax 101™, Freund Industrial Co. Ltd.) (40.0 g) and behenic acid hexa (tetra) glyceride (HB-310™, Sakamoto Yakuhin Kogyo Co. Ltd.)(30.0 g) was melted at 85° C. To this melt, 10.0 g of indolmycin, 10.0 g of acrylic polymer (HIVISWAKO 104™, Wako Pure Chemical Industries, Ltd.) and 10.0 g of partly pregelatinized starch (PCS, Asahi Kasei Industries, Ltd.) were serially added and the mixture was stirred for dispersion at a constant temperature of 85° C. for 2 hours. This molten mixture was-dropped onto a 15 cm (di.) aluminum disk rotating at 3960 rpm at a flow rate of 50 g/min, whereby 42/119-mesh spherical fine granules were obtained.

Comparative Example 3

Production of an indolmycin-containing gastrointestinal mucosa-adherent preparation A mixture of hydrogenated caster oil (Lubri wax 101™, Freund Industrial Co. Ltd.) (40.0 g) and behenic acid hexa (tetra) glyceride (HB-310™, Sakamoto Yakuhin Kogyo Co. Ltd.)(30.0 g) was melted at 85° C. To this melt, 10.0 g of indolmycin, 10.0 g of acrylic polymer (HYIVISWAKO 104™, Wako Pure Chemical Industries, Ltd.) and 10.0 g of hydroxypropyl starch (HPS, Freund Industrial Co. Ltd.) were serially added and the mixture was stirred for dispersion at a constant temperature of 85° C. for 2 hours. This molten mixture was dropped onto a 15 cm (di.) aluminum disk rotating at 3960 rpm at a flow rate of 50 g/min, whereby 42/119-mesh spherical fine granules were obtained.

Test Example 3

In vivo anti-*Helicobacter pylori* effect of the indolmycin-containing gastrointestinal mucosa-adherent preparation Mice (Crj: ICR) infected with HP were orally dosed with the indolmycin-containing gastrointestinal mucosa-adherent preparation obtained in Example 16,17 and 18 (IDM-AdMMS-16, -17 and -18 in Table 3), the indolmycin-containing gastrointestinal mucosa-adherent preparation obtained in Comparative Example 2 and 3 (IDM-AdMMS-C2 and C3 in Table 3), respectively at a dose of 30 mg/kg as indolmycin twice a day for one day. At 16 hours after the final dose, the stomach was excised and the gastric wall was homogenized and serial dilutions were plated on the HP selective medium. The inoculated medium was incubated for 4 days at 37° C. under microaerobic conditions and the number of viable cells was counted. The results are shown in Table 3.

TABLE 3

| Formulation | Dose (mg/kg) Indolmycin | Clearance rate Cleared/total (%) |
|---|---|---|
| IDM-AdMMS-C2 | 30 | 0/6 (0) |
| IDM-AdMMS-C3 | 30 | 0/6 (0) |
| IDM-AdMMS-16 | 30 | 2/6 (33) |
| IDM-AdMMS-17 | 30 | 1/7 (14) |
| IDM-AdMMS-18 | 30 | 4/11 (36) |

Compared with the IDM-containing gastrointestinal mucosa-adherent preparation containing PCS and HPS-101, IDM-containing gastrointestinal mucosa-adherent preparations containing LH-31™, LH-22 and curdlan showed higher anti-HP activity.

Test Example 4

In vivo anti-*Helicobacter pylori* effect of the indolmycin-containing gastrointestinal mucosa-adherent preparation Mongolian gerbils (MON/Jms/Gbs) infected with HP were orally dosed with indolmycin-containing gastrointestinal mucosa-adherent preparation obtained in Example 13 (IDM-AdMMS-13 in Table 4) or a 0.5% methylcellulose suspension containing indolmycin (IDM-suspension in Table 4), respectively at a dose of 1 mg/kg as indolmycin for AdMMS or 10 mg/kg as indolmycin for the suspension twice a day for seven days. At 16 hours after the final dose, the stomach was excised and the gastric wall was homogenized and serial dilutions were plated on the HP selective medium. The inoculated medium was incubated for 4 days at 37° C. under microaerobic conditions and the number of viable cells was counted. The results are shown in

TABLE 4

| Formulation | Dose (mg/kg) Indolmycin | Clearance rate Cleared/total (%) |
|---|---|---|
| Control | 0 | 0 |
| IDM-suspension | 10 | 100 |
| IDM-AdMMS-13 | 1 | 100 |

The indolmycin-containing gastrointestinal mucosa-adherent preparation showed an equivalent anti-HP effect at the dose of one tenth of the suspension.

Industrial Applicability

The mucosal medication system of the present invention is capable of attaching itself to the gastric mucosa and/or staying in the stomach to release an anti-HP agent for a potentiated bacterial elimination and exterminating action so that it is of great use in the treatment of *H. pylori* infections. Moreover, it is useful for the prophylaxis and therapy of various gastrointestinal diseases associated with *H. pylori* (e.g. gastritis, gastric ulcer, duodenal ulcer, etc.).

What is claimed is:

1. A gastrointestinal mucosa-adherent pharmaceutical composition comprising
   (A) a polyglycerol fatty acid ester, a lipid or a combination thereof,
   (B) a viscogenic agent,
   (C) low-substituted hydroxypropylcellulose and
   (D) an active ingredient,
   wherein said low-substituted hydroxypropylcellulose is contained in the range of about 1 to 30 weight %, relative to the total weight of the composition which is an effective gastrointestinal mucosa-adherent pharmaceutical composition.

2. A pharmaceutical composition according to claim 1, which is a matrix comprising a polyglycerol fatty acid ester, a lipid or a combination thereof.

3. A pharmaceutical composition according to claim 2, wherein said low-substituted hydroxypropylcellulose is dispersed.

4. A pharmaceutical composition according to claim 3, which is in granule form.

5. An anti-*Helicobacter pylori* pharmaceutical composition comprising
   (A) a polyglycerol fatty acid ester, a lipid or a combination thereof,
   (B) a viscogenic agent,
   (C) low-substituted hydroxypropylcelullose and
   (D) an effective amount of an anti-*Helicobacter pylori* substance,
   wherein said low-substituted hydroxypropylcellulose is contained in the range of about 1 to 30 weight %, relative to the total weight of the composition which is an effective gastrointestinal mucosa-adherent pharmaceutical composition.

6. An antimicrobial pharmaceutical composition comprising
   (A) a polyglycerol fatty acid ester, a lipid or a combination thereof,
   (B) a viscogenic agent,
   (C) low-substituted hydroxypropylcellulose and
   (D) an effective amount of an antimicrobial substance,
   wherein said low-substituted hydroxypropylcellulose is contained in the range of about 1 to 30 weight %, relative to the total weight of the composition which is an effective gastrointestinal mucosa-adherent pharmaceutical composition.

7. A pharmaceutical composition according to claim 1, wherein the hydroxypropoxy content of the low-substituted hydroxypropylcellulose is about 7.0 to about 13.0%.

8. A pharmaceutical composition according to claim 2, wherein the lipid is a hydrogenated castor oil.

9. A pharmaceutical composition according to claim 2, wherein the polyglycerol fatty acid ester is an ester of a polyglycerol having a degree of polymerization from 2 to 20 with a fatty acid containing 12 to 22 carbon atoms.

10. A pharmaceutical composition according to claim 2, wherein the used amount of the polyglycerol fatty acid ester and/or the lipid is 20 to 95 weight % to the total weight of the composition.

11. A pharmaceutical composition according to claim 2, wherein the used amount of the polyglycerol fatty acid ester and/or the lipid is 0.1 to 100 times by weight to the active ingredient in the composition.

12. A pharmaceutical composition according to claim 2, comprising a viscogenic agent in the matrix.

13. A pharmaceutical composition according to claim 11, wherein the used amount of the viscogenic agent is 0.5 to 30 weight % to the used weight of the composition.

14. A pharmaceutical composition according to claim 2, wherein the HLB number of the polyglycerol fatty acid ester is about 1 to about 9.

15. A pharmaceutical composition according to claim 5, wherein the used amount of the anti-*Helicobacter pylori* substance is 10 to 50 weight % to the total weight of the composition.

16. A pharmaceutical composition according to claim 2, wherein the matrix is coated with a coating material comprising a viscogenic agent.

17. A pharmaceutical composition according to claim 12 or 16, wherein the viscogenic agent is an acrylic polymer or salt thereof.

18. A pharmaceutical composition according to claim 5, wherein the anti-*Helicobacter pylori* substance is amoxicillin.

19. A pharmaceutical composition according to claim 5, wherein the anti-*Helicobacter pylori* substance is N-(diaminophosphinyl)-5-methyl-2-thiophenecarboxamide.

20. A pharmaceutical composition according to claim 5, wherein the anti-*Helicobacter pylori* substance is a tryptophanyl-t-RNA synthesis inhibitor.

21. A pharmaceutical composition according to claim 5, wherein the anti-*Helicobacter pylori* substance is a oxazolone derivative.

22. A pharmaceutical composition according to claim 5, wherein the anti-*Helicobacter pylori* substance is indolymycin.

23. A method to accelerate gastrointestinal mucosa-adherent activity of a pharmaceutical composition comprising adding low-substituted hydroxypropylcellulose to a pharmaceutical composition composition of a viscogenic agent and an active ingredient.

24. A method for modulating the adherence of a gastrointestinal mucosa-adherent composition, said method comprising adding low-substituted hydroxypropylcellulose as an accelerant of gastrointestinal mucosa-adherent activity to a gastrointestinal mucosa-adherent composition of a viscogenic agent and an active ingredient.

25. A pharmaceutical composition according to claim 2, comprising
   (i) low-substituted hydroxypropylcellulose,
   (ii) acrylic polymer or salt thereof,
   (iii) polyglycerol fatty acid ester, lipid or a combination thereof and
   (iv) an anti-*Helicobacter pylori* substance.

26. A pharmaceutical composition according to claim 25, wherein (i) the hydroxypropoxy content of said low-substituted hydroxypropylcellulose is about 7.0 to about 13.0%, (ii) the molecular weight of the acrylic polymer is about $20 \times 10^4$ to about $600 \times 10^4$, (iii) the polyglycerol fatty acid ester is tetraglycerol polyricinolate, and (iv) the anti-*Helicobacter pylori* substance is indolmycin.

27. A pharmaceutical composition according to claim 2, comprising (i) about 1 to about 20 parts by weight of said low-substituted hydroxypropylcellulose, whose hydroxypropoxy content is about 7.0 to about 13.0%, (ii) about 1 to about 20 parts by weight of acrylic polymer or salt thereof, whose molecular weight is about $20 \times 10^4$ to about $600 \times 10^4$, (iii) about 40 to about 90 parts by weight of behenic acid hexa(tetra)glyceride, tetraglycerol polyricinolate or a combination thereof, and (iv) about 5 to about 40 parts by weight of indolmycin.

* * * * *